(12) United States Patent
Muratake et al.

(10) Patent No.: US 8,895,769 B2
(45) Date of Patent: Nov. 25, 2014

(54) SILICON-CONTAINING CARBOXYLIC ACID DERIVATIVE

(75) Inventors: Hideaki Muratake, Tokyo (JP); Ai Ito, Tokyo (JP); Koichi Shudo, Tokyo (JP)

(73) Assignee: Kemphys Ltd., Tokyo (JP)

( * ) Notice: Subject to any disclaimer, the term of this patent is extended or adjusted under 35 U.S.C. 154(b) by 0 days.

(21) Appl. No.: 14/112,087

(22) PCT Filed: Apr. 19, 2012

(86) PCT No.: PCT/JP2012/060552
§ 371 (c)(1),
(2), (4) Date: Oct. 16, 2013

(87) PCT Pub. No.: WO2012/144551
PCT Pub. Date: Oct. 26, 2012

(65) Prior Publication Data
US 2014/0031575 A1    Jan. 30, 2014

(30) Foreign Application Priority Data
Apr. 20, 2011  (JP) .................................. 2011-093714

(51) Int. Cl.
*C07F 7/08* (2006.01)
*C07F 7/10* (2006.01)

(52) U.S. Cl.
CPC ............... *C07F 7/0818* (2013.01); *C07F 7/082* (2013.01); *C07F 7/0816* (2013.01)
USPC .......................................... 556/438; 556/413

(58) Field of Classification Search
CPC ........... C07F 7/10; C07F 7/0818; C07F 7/082
USPC .................. 556/416, 418, 438, 413
See application file for complete search history.

(56) References Cited

U.S. PATENT DOCUMENTS

| | | | |
|---|---|---|---|
| 2,628,245 A * | 2/1953 | Speier, Jr | 556/437 |
| 2,805,237 A | 9/1957 | Kiffer et al. | |
| 3,825,546 A | 7/1974 | Rice et al. | |
| 5,563,175 A | 10/1996 | Silverman et al. | |
| 5,616,793 A | 4/1997 | Huckabee et al. | |
| 5,629,447 A | 5/1997 | Huckabee et al. | |
| 5,637,767 A | 6/1997 | Grote et al. | |
| 5,840,956 A | 11/1998 | Grote et al. | |

FOREIGN PATENT DOCUMENTS

| | | |
|---|---|---|
| GB | 2397576 | 7/2004 |
| JP | 48-34166 | 5/1973 |

OTHER PUBLICATIONS

Verma et al., "Desymmetrization of prochiral anhydrides with Evans' oxazolidinones: an efficient route to homochiral glutaric and adipic acid derivatives," J. Chem. Soc., Perkin Trans. I, 1999, 257-264.*
Verma et al., "Desymmetrization of 3-dimethyl(phenyl)silyl glutaric anhydride with Evans' oxazolidinone: an application to stereocontrolled synthesis of the antifungal agent (+)-preussin," J. Chem. Soc., Perkin Trans. 1, 1999, 265-270.*
Journal of Organometallic Chemistry, 690, 2005, pp. 678-684.
Burgess, K. et al., "Optically Active Building Blocks from the SPAC Reaction: A Completely Asymmetric Synthesis of (4S-cis)-5-(Cyclohexylmethyl)-4-hydroxy-2-pyrrolidinone", a Statine Analogue, Journal of Organic Chemistry, vol. 56, No. 6, 1991, pp. 2050-2058.
Verma, R. et al., "A silicon controlled total synthesis of the antifungal agent (+)—preussin", Chemical Communications, No. 17, 1997, pp. 1601-1602.
International Search Report in PCT/JP2012/060552, mail date is Jul. 17, 2012.
International Preliminary Report on Patentability for PCT/JP2012/060552, mail date is Oct. 31, 2013.
Extended European Search Report issued with respect to application No. 12774607.1, mail date is Aug. 25, 2014.
Siverman R., "3-Alkyl-4-aminobutyric Acids: The first Class of Anticonvulsant Agents That Activates L-Glutamic Acid Decarboxylase", Journal of Medicinal Chemistry, vol. 34, No. 7, 1991, pp. 2295-2298.
Rodriguez V., "The 5-exo-trig radical cyclization reaction under reductive and oxidative conditions in the synthesis of optically pure GABA derivatives", Tetrahedron, vol. 60, No. 48, 2004, pp. 10809-10815.

* cited by examiner

*Primary Examiner* — Paul A Zucker
*Assistant Examiner* — Mark Luderer
(74) *Attorney, Agent, or Firm* — Greenblum & Bernstein, P.L.C.

(57) ABSTRACT

A compound represented by the formula (I) [$R^1$ to $R^3$ represent an alkyl group, an alkenyl group, and the like; n represents 0 or 1; $R^4$ represents an amino group or —$(CX_2)_m$—COOH (m represents 0 to 3, and X represents hydrogen atom); $R^5$ represents —$(CY_2)_p$—COOR$^6$ (p represents an 0 to 3, Y represents hydrogen atom, and $R^6$ represents hydrogen atom or an alkyl group)], or a salt thereof.

(I)

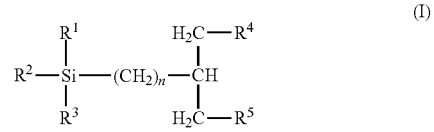

3 Claims, No Drawings

SILICON-CONTAINING CARBOXYLIC ACID DERIVATIVE

TECHNICAL FIELD

The present invention relates to a silicon-containing carboxylic acid derivative.

BACKGROUND ART

Carboxyl group is one of important functional groups in pharmaceutical compounds, and is widely used in combination with various functional groups, such as amino group, hydroxyl group, and a halogen atom. For example, gabapentin (2-[1-(aminomethyl)cyclohexyl]acetic acid) used an anti-epileptic, and pregabalin ((S)-3-(aminomethyl)-5-methyl-hexanoic acid) used for peripheral neuropathic pains (postherpetic neuralgia and the like) are examples of medicaments having carboxyl group and amino group in combination.

There have been proposed pharmaceutical compounds consisting of a carboxylic acid derivative in which a carbon atom is replaced with a silicon atom. For example, a β-carbonylsilane compound having a silicon atom as a ring-constituting atom in a ring system such as 6-membered ring has been proposed as an analogue of gabapentin (GB 2,397,576A), and it is taught that this compound can be used as a pharmaceutical compound (Journal of Organometallic Chemistry, 690, pp. 678-684, 2005, with reference to the method for preparation of this compound). However, any compounds corresponding to pregabalin of which carbon atom in the fundamental structure thereof is replaced with a silicon atom are not known.

Prior Art References

Patent Document
Patent document 1: GB 2,397,576A
Non-Patent Document
Non-patent document 1: Journal of Organometallic Chemistry, 690, pp. 678-684, 2005

SUMMARY OF THE INVENTION

Object to be Achieved by the Invention

An object of the present invention is to provide a novel silicon-containing carboxylic acid derivative useful as an active ingredient of medicaments, and the like.

Means for Achieving the Object

The inventors of the present invention conducted various researches to provide a novel silicon-containing carboxylic acid derivative, and as a result, they found that compounds represented by the following general formula (I) were useful as active ingredients of medicaments and the like, and accomplished the present invention.

The present invention thus provides a compound represented by the following general formula (I):

[Formula 1]

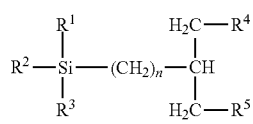

(I)

[wherein, $R^1$, $R^2$, and $R^3$ independently represent an alkyl group, an alkenyl group, an alkynyl group, or an aryl group (these alkyl group, alkenyl group, alkynyl group and aryl group may have a substituent), two or three groups selected from $R^1$, $R^2$, and $R^3$ may bind together to form a ring; n represents 0 or 1; $R^4$ represents an amino group (this amino group may have a substituent) or —$(CX_2)_m$—COOH (m represents an integer of 0 to 3, and X represents hydrogen atom or deuterium atom); $R^5$ represents —$(CY_2)_p$—$COOR^6$ (p represents an integer of 0 to 3, Y represents hydrogen atom or deuterium atom, and $R^6$ represents hydrogen atom or an alkyl group (this alkyl group may have a substituent))], or a salt thereof.

According to a preferred embodiment of the aforementioned invention, there is provided the aforementioned compound or a salt thereof, wherein $R^1$, $R^2$, and $R^3$ are independently an alkyl group or an aryl group, n is 0 or 1, $R^4$ is an amino group, a monoalkylamino group, or an acylamino group, and $R^5$ is —$(CH_2)_p$—$COOR^6$ (p represents an integer of 0 to 3, and $R^6$ is hydrogen atom or an alkyl group).

As another aspect, the present invention provides a medicament containing a compound represented by the aforementioned general formula (I) or a physiologically acceptable salt thereof as an active ingredient.

The present invention also provides use of a compound represented by the aforementioned general formula (I) or a physiologically acceptable salt thereof for manufacture of the aforementioned medicament; and a method for prophylactic and/or therapeutic treatment of a disease of a mammal including human, which comprises the step of administering a prophylactically and/or therapeutically effective amount of a compound represented by the aforementioned general formula (I) or a physiologically acceptable salt thereof to a mammal including human.

Effect of the Invention

The compounds represented by the aforementioned general formula (I) and salts thereof provided by the present invention can be used as, for example, an active ingredient of medicaments. They have superior stability in vivo, and are useful as an active ingredient of medicaments with a sustained metabolic rate.

Modes for Carrying out the Invention $R^1$, $R^2$, and $R^3$ independently represent an alkyl group, an alkenyl group, an alkynyl group, or an aryl group. In this specification, the alkyl group includes a linear alkyl group, a branched alkyl group, a cyclic alkyl group, and an alkyl group consisting of a combination of the foregoing alkyl groups. Although number of carbon atom of the alkyl group is not particularly limited, it is, for example, about 1 to 18, preferably about 1 to 12, more preferably about 1 to 6, particularly preferably about 1 to 4. In this specification, the alkenyl group includes a linear alkenyl group, a branched alkenyl group, a cyclic alkenyl group, and an alkenyl group consisting of a combination of the foregoing alkenyl groups. Although number of carbon atoms of the alkenyl group is not particularly limited, it is, for example, about 2 to 18, preferably about 2 to 12, more preferably about 2 to 6, particularly preferably about 2 to 4. Number of double bond contained in the alkenyl group is, for example, about 1 to 3, preferably about 1 or 2, particularly preferably about 1. In this specification, the alkynyl group includes a linear alkynyl group, and a branched alkynyl group. Although number of carbon atoms of the alkynyl group is not particularly limited, it is, for example, about 2 to 18, preferably about 2 to 12, more preferably about 2 to 6, particularly preferably about 2 to 4. Number of triple bond contained in the alkynyl group is, for example, about 1 to 3, preferably about 1 or 2, particularly preferably about 1. The alkenyl group may contain about 1 or 2 triple bonds.

In this specification, the aryl group includes an aromatic hydrocarbon group as well as an aromatic group containing a heteroatom as a ring-constituting atom. The aryl group may be a monocyclic aryl group or a condensed polycyclic aryl group. When a heteroatom is contained as a ring-constituting atom, nitrogen atom, oxygen atom, or sulfur atom can be used as the heteroatom. Examples of the aryl group containing a heteroatom as a ring-constituting atom include, for example, pyridyl group, pyrimidinyl group, imidazolyl group, indolyl group, quinolyl group, phthalazinyl group, naphthyridinyl group, pyrrolyl group, thienyl group, furyl group, furazanyl group, and the like, but are not limited to these examples. As the monocyclic aryl group, for example, a 5- to 7-membered aryl group is preferred. As the aryl group, an aromatic hydrocarbon group is preferred, and phenyl group is more preferred.

The alkyl group, the alkenyl group, the alkynyl group, and the aryl group represented by $R^1$, $R^2$ or $R^3$ may have one or two or more substituents. When they have two or more substituents, they may be the same or different. Substitution position of the substituent is not particularly limited, and the alky group may have one or more substituents at arbitrary position(s). When the alkyl group, the alkenyl group, the alkynyl group, or the aryl group represented by $R^1$, $R^2$ or $R^3$ has a substituent, examples of the substituent include, for example, a halogen atom (fluorine atom, chlorine atom, bromine atom, or iodine atom), hydroxyl group, oxo group, carboxyl group, an alkoxycarbonyl group, an acyl group, amino group, an alkyl group, an alkenyl group, an alkynyl group, an alkoxyl group, an aryl group, an aralkyl group, and the like, but are not limited to these examples. These substituents may be further substituted with another substituent. Examples of the substituent of such a case include, for example, a fluoroalkyl group, fluoroacetyl group, methoxybenzyl group, and the like, but are not limited to these examples.

Two or three groups selected from $R^1$, $R^2$, and $R^3$ may bind together to form a ring. Although size of the ring formed is not particularly limited, it is, for example, an about 4- to 8-membered ring, preferably an about 5- to 7-membered ring. For example, $R^1$ and $R^2$ may bind together to form a 5- or 6-membered ring, or $R^1$, $R^2$, and $R^3$ may bind together to form a bicyclo ring (for example, such a bicyclo ring as bicyclo [2.2.2] structure and bicyclo[3.2.2] structure).

It is preferred that $R^1$, $R^2$, and $R^3$ independently represent an alkyl group or an aryl group. It is more preferred that $R^1$, $R^2$, and $R^3$ independently represent an alkyl group having about 1 to 6 carbon atoms, and for example, it is preferred that RI and $R^2$ are methyl groups, and $R^3$ is isopropyl group or tert-butyl group. Further, it is also preferred that one to three of $R^1$, $R^2$, and $R^3$ are aryl groups, for example, phenyl groups. When one or two of $R^1$, $R^2$, and $R^3$ are aryl groups, for example, phenyl groups, it is preferred that the remaining group(s) is(are) an alkyl group or alkyl groups having about 1 to 6 carbon atoms.

Symbol n represents 0 or 1, and it is preferred that n is 0. When n is 0, it is meant that methylene group does not exist.

$R^4$ represent an amino group or $-(CX_2)_m-COOH$. The amino group represented by $R^4$ may have one or two substituents. As the substituent, for example, an alkyl group, an alkenyl group, an alkynyl group, an aryl group, an acyl group (for example, an alkanoyl group such as acetyl group, an aroyl group such as benzoyl group, and the like), and the like can be used, but the substituent is not limited to these examples. Further, examples of the amino group substituted with an acyl group include an acylamino group formed by amino group and carboxyl group of an amino acid bound with an amide bond (for example, see, International Patent Publication WO02/100344, and the like), a carbamate group (for example, one formed by binding (2-methyl-1-oxopropyloxy) ethoxycarbonyl group with amino group), and the like, but are not limited to these examples. Modification of the amino group with these acyl groups is useful for use as a prodrug, sustained release preparation, or the like. The amino group represented by $R^4$ preferably does not have a substituent, or has one alkyl group or acyl group. When the amino group has one alkyl group, number of carbon atoms of the alkyl group is about 1 to 6.

In the group represented as $-(CX_2)_m-COOH$ as $R^4$, m represents an integer of 0 to 3, and m is preferably 1 or 2, more preferably 1. X represents hydrogen atom or deuterium atom. When X is deuterium atom, it is meant that substitution ratio of deuterium (ratio of hydrogen atoms replaced with deuterium atoms) is at least 50%, preferably 70% or higher, more preferably 80% or higher, particularly preferably 90% or higher, most preferably 95% or higher, and it is not necessary that hydrogen atoms are completely replaced with deuterium atoms. Therefore, the expression that X is deuterium atom should be construed to include a case that a part of X consists of hydrogen atoms. As $R^4$, an amino group is preferred, and the amino group is preferably unsubstituted amino group or a monoalkylamino group.

In the group represented as $-(CY_2)_p-COOR^6$ as $R^5$, p represents an integer of 0 to 3, and p is preferably 1 or 2, more preferably 1. Symbol Y represents hydrogen atom or deuterium atom, and the explanation for X is similarly applied to Y. $R^6$ represents hydrogen atom or an alkyl group, and the alkyl group represented by $R^6$ may have a substituent. Examples of the substituent include, for example, a halogen atom (fluorine atom, chlorine atom, bromine atom, or iodine atom), hydroxyl group, oxo group, carboxyl group, an alkoxycarbonyl group, an acyl group, amino group, an alkyl group, an alkenyl group, an alkynyl group, an alkoxyl group, an aryl group, an aralkyl group, and the like, but are not limited to these examples. These substituents may be further substituted with another substituent. Examples of another substituent include, for example, a fluoroalkyl group, methoxymethyl group, ethoxymethyl group, and the like, but are not limited to these examples.

Specific examples of the ester group, which is formed when $R^6$ is the alkyl group which may be substituted, include, for example, methyl group, ethyl group, propyl group, isopropyl group, butyl group, isobutyl group, t-butyl group, benzyl group, acetoxymethyl group, 1-(acetoxy)ethyl group, propionyloxymethyl group, 1-(propionyloxy)ethyl group, butyryloxymethyl group, 1-(butyryloxy)ethyl group, isobutyryloxymethyl group, 1-(isobutyryloxy)ethyl group, valeryloxymethyl group, 1-(valeryloxy)ethyl group, isovaleryloxymethyl group, 1-(isovaleryloxy)ethyl group, pivaloyloxymethyl group, 1-(pivaloyloxy)ethyl group, methoxycarbonyloxymethyl group, 1-(methoxycarbonyloxy) ethyl group, ethoxycarbonyloxymethyl group, 1-(ethoxycarbonyloxy)ethyl group, propoxycarbonyloxymethyl group, 1-(propoxycarbonyloxy)ethyl group, isopropoxycarbonyloxymethyl group, 1-(isopropoxycarbonyloxy)ethyl group, butoxycarbonyloxymethyl group, 1-(buthoxycarbonyloxy) ethyl group, isobutoxycarbonyloxymethyl group, 1-(isobuthoxycarbonyloxy)ethyl group, t-buthoxycarbonyloxymethyl group, 1-(t-buthoxycarbonyloxy)ethyl group, cyclopentanecarbonyloxymethyl group, 1-(cyclopentanecarbonyloxy)ethyl group, cyclohexanecarbonyloxymethyl group, 1-(cyclohexanecarbonyloxy)ethyl group, cyclopenthyloxycarbonyloxymethyl group, 1-(cyclopenthyloxycarbonyloxy)ethyl group, cyclohexyloxycarbonyloxymethyl group, 1-(cyclohexyloxycarbonyloxy)ethyl group, benzoyloxymethyl group, 1-(benzoyloxy)ethyl group, phenoxycarbonyloxymethyl group, 1-(phenoxycarbonyloxy)ethyl group, (5-methyl-2-oxo-1,3-dioxolen-4-yl)methyl group, 2-trimethylsilylethyl group, and the like, but are not limited to these examples.

The compounds represented by the general formula (I) may form an acid addition salt or a base addition salt. Examples of the acid addition salt include, for example, mineral acid salts such as hydrochloride, sulfate, and nitrate, organic acid salts such as p-toluenesulfonate, oxalate, and malate, and the like, but are not limited to these examples. Examples of the base addition salt include, for example, metal salts such as sodium salt, potassium salt, magnesium salt, and calcium salt, ammonium salts, organic amine salts such as triethylamine salt and ethanolamine salt, and the like, but are not limited to these examples. Among these salts, physiologically acceptable salts are preferred, when the compounds of the present invention are used as an active ingredient of medicaments.

Further, the compounds represented by the general formula (I) may have one or two or more asymmetric carbons depending on the type of substituent, and arbitrary optical isomers based on these asymmetric carbons, arbitrary mixtures of optical isomers, racemates, diastereoisomers based on two or more asymmetric carbons, arbitrary mixtures of diastereoisomers, and the like are all encompassed within the scope of the present invention. When the compounds represented by the general formula (I) contain a double bond, geometrical isomers thereof may exist, and Z-isomers and E-isomers in pure forms, as well as mixture of them at arbitrary ratios are also encompassed within the scope of the present invention. Furthermore, arbitrary hydrates or solvates of the free compounds and salts thereof are also encompassed within the scope of the present invention.

The compounds of the present invention represented by the general formula (I) can be synthesized by the methods specifically described in the examples of this specification. Since synthesis methods of β-carbonylsilanes, having a carbon atom instead of a silicon atom, have been reported (for example, GB 2,397,576A and Journal of Organometallic Chemistry, 690, pp. 678-684, 2005), those skilled in the art can easily prepare arbitrary compounds of the general formula (I) by referring to the synthetic methods specifically described in the examples of this specification together with the aforementioned publications. Further, as for the synthetic method of the compounds having an amino acid and carboxyl group, for example, the synthesis methods of pregabalin and analogues thereof (U.S. Pat. Nos. 5,563,175, 5,840,956, 5,637,767, 5,629,447, 5,616,793, 5,563,175, and the like) can also be referred to.

Although the use of the compounds of the present invention represented by the general formula (I) is not particularly limited, they can be used as, for example, active ingredients of medicaments. Examples of use of the medicaments include, for example, prophylactic and/or therapeutic treatment of epilepsy, pains, inflammations, gastrointestinal disorders, insomnia, mental disorders, diabetic peripheral nerve disorders, and the like, but are not limited to these examples. Among the compounds of the present invention, the compounds having an amino acid and carboxyl group are expected to have the same pharmacological actions as those of, for example, pregabalin or gabapentin, and therefore they can be used for the specific uses described in, for example, International Patent Publication WO2010/017498, paragraph [0003] and the like The entire disclosure of the aforementioned patent document is incorporated into the disclosure of this specification by reference.

When a compound of the present invention represented by the general formula (I) or a physiologically acceptable salt thereof is used as a medicament, the compound, physiologically acceptable salt thereof, or a hydrate or solvate thereof per se may be administered to a mammal including human, but it can be preferably administered as a pharmaceutical composition for oral or parenteral administration that can be prepared by a method well known to those skilled in the art. Examples of the pharmaceutical composition suitable for oral administration include, for example, tablets, capsules, powders, subtilized granules, granules, solutions, syrups, and the like, and examples of the pharmaceutical composition suitable for parenteral administration include, for example, injections, fusion drips, suppositories, inhalants, eye drops, nose drops, ointments, creams, patches, transdermal preparations, transmucosal preparations, and the like.

For the preparation of these pharmaceutical compositions, one or two or more kinds of pharmaceutical additives available for those skilled in the art can be used. Examples of the pharmaceutical additives include, for example, excipients, disintegrating agents or disintegrating aids, binders, lubricants, coating agents, dyes, diluents, bases, dissolving agents or dissolving aids, isotonic agents, pH modifiers, stabilizers, propellants, tackifiers, and the like, and these can be appropriately chosen by those skilled in the art according to the form of the pharmaceutical composition, and two or more kinds of them may be used in combination. Dose of the medicament is not particularly limited, and can be appropriately determined depending on various factors which should usually be taken into consideration, such as weight and age of patients, type and symptoms of disease, and administration route. For example, in the case of oral administration, the compound or a salt thereof can be used in an amount in the range of about 0.001 to 10,000 mg per day for adults.

EXAMPLES

Hereafter, the present invention will be still more specifically explained with reference to examples. However, the scope of the present invention is not limited to the following examples.

Example 1

Preparation of benzyl 3-(trimethylsilyl)acrylate

[Formula 2]

A solution of 3-trimethylsilylacrylic acid (510 mg, 3.54 mmol) [J. Org. Chem., 56, pp. 4766-4772, 1991] in dichloromethane (8 ml) was added successively with benzyl alcohol (0.59 ml, 5.71 mmol), dicyclohexylcarbodiimide (DCC, 914 mg, 4.44 mmol) and 4-dimethylaminopyridine (4-DMAP, 43 mg, 0.352 mmol) under ice cooling, the mixture was stirred for 5 minutes, and then stirring was further continued at room temperature for 16 hours. The reaction mixture was cooled on ice, and then added with aqueous hydrochloric acid (1 N, 5 ml), the mixture was filtered under reduced pressure, and the resulting urea was washed with ethyl acetate. After the layers were separated, the organic layer was washed with saturated aqueous sodium hydrogencarbonate and water, and dried over anhydrous sodium sulfate, and the solvent was evaporated. The residue was purified by silica gel chromatography [hexane/ethyl acetate (24:1)] to obtain benzyl 3-trimethylsilylacrylate (782 mg, 94%) mentioned in the title as colorless oil.

HRMS: Calcd for $C_{13}H_{18}O_2Si$: 234.1075, Found: 234.1065

MS (m/z): 234 ($M^+$, 0.5), 219 (6), 144 (17), 127 (13), 91 (100), 73 (28), 69 (30)

IR (neat) $cm^{-1}$: 1720

$^1$H-NMR ($CDCl_3$) δ: 0.13 (9H, s), 5.19 (2H, s), 6.29 (1H, d, J=18.5 Hz), 7.31 (1H, d, J=18.5 Hz), 7.31-7.43 (5H, m)

Example 2

Preparation of benzyl 3-(tert-butyldimethylsilyl)acrylate

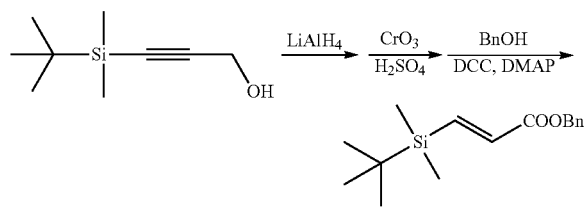

A solution of 3-(tert-butyldimethylsilyl)-2-propyn-1-ol (4.66 g, 27.4 mmol) [Helv. Chim. Acta, 85, pp. 4165-4181, 2002] in tetrahydrofuran (THF, 35 ml) cooled on ice was added portionwise with lithium aluminum hydride (1.25 g, 32.9 mmol) under an argon atmosphere, the mixture was stirred for 1 hour, and then stirring was further continued at room temperature for 21 hours. The reaction mixture was poured into ammonium chloride/water/ice, and the entire mixture was filtered thorough Celite. The Celite layer was washed with ethyl acetate, then the washing solvent was combined with the filtrate, the combined organic layer was washed with water, and dried over anhydrous sodium sulfate, and the solvent was evaporated to obtain a residue (4.38 g). This residue was dissolved in acetone (70 ml), and the solution was added with a solution of chromic acid (4.93 g, 49.3 mmol) in 30% aqueous sulfuric acid (20.6 ml) under ice cooling with washing the vessel with acetone (10 ml). The reaction mixture was further stirred at 0° C. for 30 minutes, and then stirring was continued at room temperature for 15.5 hours. The reaction mixture was poured into water, the mixture was added with ethyl acetate, the solid matter was sufficiently pulverized, and the layers were separated. The organic layer was washed with water, and dried over anhydrous sodium sulfate, and the solvent was evaporated to obtain a crystalline carboxylic acid (4.94 g). A solution of the resulting crude carboxylic acid in dichloromethane (40 ml) was subjected to benzyl esterification according to the method of Example 1, and the resulting reaction mixture (9.90 g) was subjected to purification by silica gel chromatography [hexane/ethyl acetate (49:1)] to obtain benzyl 3-(tert-butyldimethylsilyl)acrylate (5.79 g, 76% in total) mentioned in the title as colorless oil.

HRMS: Calcd for $C_{16}H_{24}O_2Si$: 276.1544, Found: 276.1528

MS (m/z): 276 ($M^+$, 0.4), 219 (45), 165 (2), 129 (11), 91 (100), 75 (10), 73 (15), 69 (12), 41 (12)

IR (neat) $cm^{-1}$: 1721

1H-NMR ($CDCl_3$) 67: 0.09 (6H, s), 0.90 (9H, s), 5.20 (2H, s), 6.31 (1H, d, J=19 Hz), 7.30-7.42 (5H, m), 7.33 (1H, d, J=19 Hz)

Example 3

Preparation of benzyl 3-(dimethylphenylsilyl)acrylate

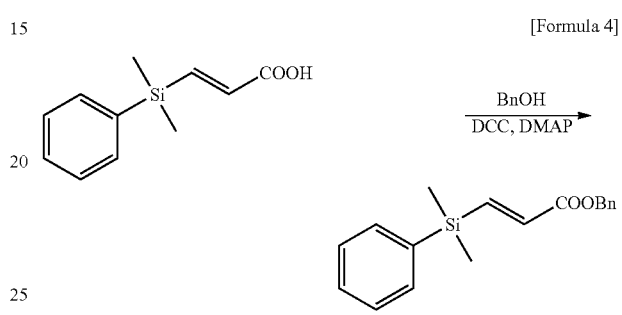

In the same manner as that of Example 1, benzyl 3-(dimethylphenylsilyl)-acrylate (1.39 g, 72%) mentioned in the title was obtained as colorless oil from 3-(dimethylphenylsilyl)acrylic acid (1.34 g, 6.48 mmol).

$^1$H-NMR ($CDCl_3$) δ: 0.41 (6H, s), 5.18 (2H, s), 6.31 (1H, d, J=19 Hz), 7.30-7.55 (11H, m)

Example 4

Preparation of benzyl 3-(dimethyl-n-octylsilyl)acrylate

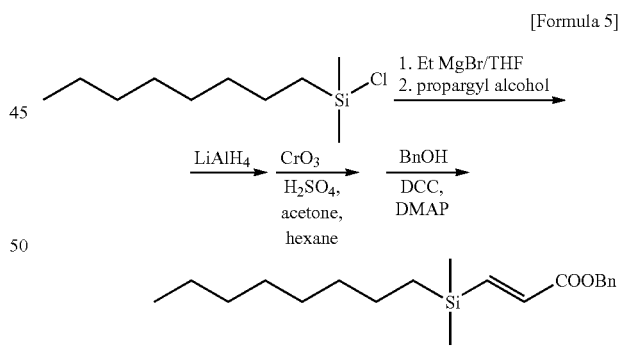

A suspension of magnesium (Mg, 1.34 g, 55.8 mg atom) in THF (20 ml) was slowly added dropwise with ethyl bromide (4.18 ml, 56.0 mmol) at room temperature, and the mixture was stirred until Mg was dissolved. The reaction mixture was slowly added dropwise with a solution of 2-propyn-1-ol (1.16 ml, 20.0 mmol) in THF (5 ml) under ice cooling, and the mixture was further stirred at room temperature for 15 hours. The reaction mixture was added dropwise with dimethyl-n-octylchlorosilane (13.3 ml, 56.0 mmol) under ice cooling, and then the mixture was further refluxed by heating for 2.5 hours. The reaction mixture was slowly added with diluted sulfuric acid (ca. 7%, 21.6 ml) with stirring under ice cooling, and the mixture was extracted with ethyl acetate. The organic layer was washed with saturated aqueous sodium hydrogencarbonate and water, and dried over anhydrous sodium sulfate, and the solvent was evaporated. The residue was purified by silica gel chromatography [hexane->hexane/ethyl acetate (10:1)] to obtain colorless oil (4.51 g, quant.). A solution of a part of this product (4.27 g, 18.9 mmol) in THF (20 ml) was reduced with LiAlH$_4$ according to the method of Example 2 to obtain a residue (3.72 g). A part of this residue (3.51 g, 15.4 mmol) was oxidized with chromic acid/sulfuric acid using a 20% hexane/acetone solution as a solvent according to the method of Example 2. The resultant was purified by column chromatography [hexane/ethyl acetate (6:1)] to obtain a carboxylic acid (2.24 g, 60%). A part of this product (1.32 g, 5.44 mmol) was treated according to the method of Example 2 to obtain benzyl 3-(dimethyl-n-octylsilyl)acrylate (1.39 g, 51%) mentioned in the title as colorless oil.

$^1$H-NMR (CDCl$_3$) δ: 0.10 (6H, s), 0.60 (2H, br t, J=7.5 Hz), 0.88 (3H, br t, J=7 Hz), 1.14-1.36 (12H, m), 5.19 (2H, s), 6.28 (1H, d, J=18.5 Hz), 7.31 (1H, d, J=18.5 Hz), 7.30-7.42 (5H, m)

Example 5

Preparation of benzyl 4-nitro-3-(trimethylsilyl)butanoate

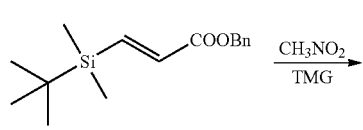

[Formula 6]

A solution of benzyl 3-(trimethylsilyl)acrylate (782 mg, 3.34 mmol) in nitromethane (3 ml) was added with N,N,N',N'-tetramethylguanidine (105 μl, 0.838 mmol) at room temperature, and the mixture was stirred for 15 hours. The reaction mixture was added with aqueous hydrochloric acid (1 N), and the mixture was extracted with ethyl acetate. The organic layer was washed with saturated aqueous sodium hydrogencarbonate and water, and dried over anhydrous sodium sulfate, and the solvent was evaporated. The residue was purified by silica gel chromatography [hexane/ethyl acetate (14:1)] to obtain benzyl 4-nitro-3-(trimethylsilyl)butanoate (863 mg, 88%) mentioned in the title as colorless oil.

MS (m/z): 280 (M$^+$-Me, 0.2), 224 (8), 143 (8), 99 (12), 91 (100), 73 (29), 56 (48), 41 (21)

IR (neat) cm$^{-1}$: 1730, 1547

$^1$H-NMR (CDCl$_3$) δ: 0.07 (9H, s), 1.96-2.06 (1H, m), 2.49 (1H, dd, J=16.5, 7 Hz), 2.56 (1H, dd, J=16.5, 5.5 Hz), ca. 4.44-4.54 (2H, m), 5.10 (2H, s), 7.29-7.41 (5H, m)

Example 6

Preparation of benzyl 4-nitro-3-(tert-butyldimethylsilyl)butanoate

[Formula 7]

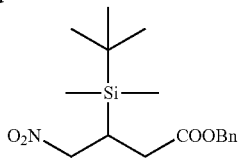

In the same manner as that of Example 5, benzyl 4-nitro-3-(tert-butyldimethylsilyl)butanoate mentioned in the title was obtained as colorless oil (561 mg, 79%) from benzyl 3-(tert-butyldimethylsilyl)acrylate (580 mg, 2.10 mmol).

MS (m/z): 280 (M$^+$-tert-Bu, 9), 143 (18), 117 (14), 115 (24), 104 (64), 99 (34), 91 (100), 75 (98), 73 (96), 65 (95), 59 (93), 57 (94), 45 (54), 43 (55), 41 (94)

IR (neat) cm$^{-1}$: 1730, 1549

$^1$H-NMR (CDCl$_3$) δ: 0.01 (3H, s), 0.04 (3H, s), 0.93 (9H, s), 2.15 (1H, dddd, J=10.5, 6.5, 5, 4.5 Hz), 2.52 (1H, dd, J=17.5, 6.5 Hz), 2.63 (1H, dd, J=17.5, 5 Hz), 4.50 (1H, dd, J=13.5, 4.5 Hz), 4.57 (1H, dd, J=13.5, 10.5 Hz), 5.11 (2H, s), 7.32-7.39 (5H, m)

Example 7

Preparation of benzyl 4-nitro-3-(dimethylphenylsilyl)butanoate

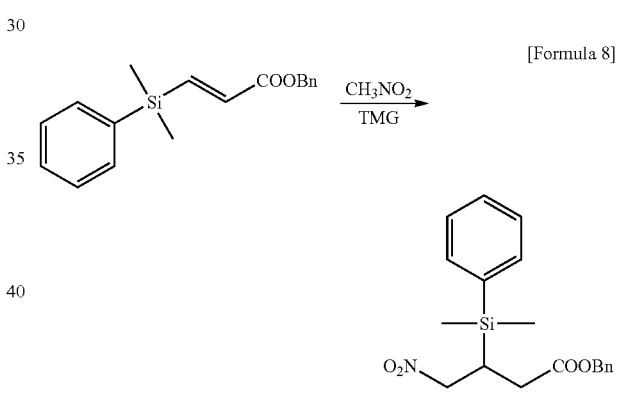

[Formula 8]

In the same manner as that of Example 5, benzyl 4-nitro-3-(dimethylphenylsilyl)butanoate (543 mg, 34%) mentioned in the title was obtained as colorless oil from benzyl 3-(dimethylphenylsilyl)acrylate (1.33 g, 4.50 mmol).

$^1$H-NMR (CDCl$_3$) δ: 0.37 (6H, s), 2.20-2.32 (1H, dddd, J=7, 7, 7, 5.5 Hz), 2.45 (1H, dd, J=17, 7 Hz), 2.56 (1H, dd, J=17, 5.5 Hz), 4.42 (2H, J=7 Hz), 5.04 (2H, s), 7.26˜7.50 (10H, m)

Example 8

Preparation of benzyl 4-nitro-3-(dimethyl-n-octylsilyl)butanoate

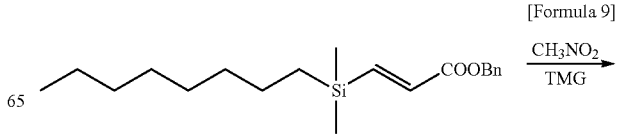

[Formula 9]

-continued

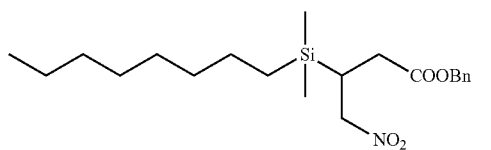

In the same manner as that of Example 5, benzyl 4-nitro-3-(dimethyl-n-octylsilyl)butanoate (497 mg, 73%) mentioned in the title was obtained as colorless oil from benzyl 3-(dimethyl-n-octylsilyl)acrylate (796 mg, 2.40 mmol).

$^1$H-NMR (CD$_3$OD) δ: 0.02 (3H, s), 0.04 (3H, s), 0.57 (1H, br t, J=8 Hz), 0.89 (3H, br t, J=7 Hz), 1.26-1.38 (12H, m), 1.98-2.10 (1H, m), 2.48 (1H, dd, J=16.5, 7 Hz), 2.54 (1H, dd, J=16.5, 5.5 Hz), 4.50 (1H, dd, J=13.5, 10 Hz), 4.56 (1H, dd, J=13.5, 4 Hz), 5.08 (2H, s), 7.27-7.40 (5H, m)

Example 9

Preparation of 4-amino-3-(trimethylsilyl)butanoic acid

[Formula 10]

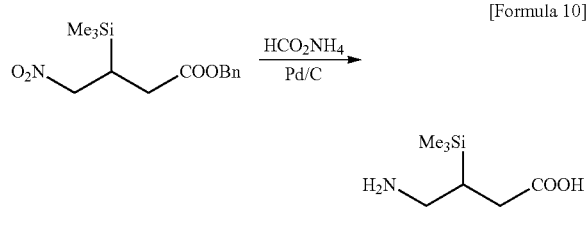

A suspension of benzyl 4-nitro-3-(trimethylsilyl)butanoate (797 mg, 2.70 mmol) and palladium/carbon (10%, 165 mg) in methanol (30 ml) was added with ammonium formate (1.70 g, 27.0 mmol), and the mixture was stirred under an argon atmosphere for 40 hours. The reaction mixture was filtered through Celite, and the Celite layer was washed with methanol. The reaction mixture was concentrated under reduced pressure, and the residue was purified by recrystallization and silica gel chromatography [methanol (10 to 25%)/chloroform] to obtain 4-amino-3-(trimethylsilyl)butanoic acid (406 mg, 86%) mentioned in the title as colorless powder.

Mp: 199 to 201° C. (methanol/2-propanol)

HRMS: Calcd for C$_7$H$_{17}$NO$_2$Si: 175.1028, Found: 175.1057

MS (m/z): 175 (M$^+$, 0.3), 156 (20), 143 (8), 116 (10), 99 (H), 75 (49), 73 (100), 59 (18), 45 (29), 43 (25), 41 (19)

IR (KBr) cm$^{-1}$: 1651

$^1$H-NMR (CD$_3$OD) δ: 0.07 (9H, s), 1.23 (1H, dddd, J=11, 11, 2, 1.5 Hz), 2.26 (1H, dd, J=16.5, 11 Hz), 2.56 (1H, ddd, J=16.5, 2, 1 Hz), 2.82 (1H, dd, J=13, 11 Hz), 3.16 (1H, ddd, J=13, 1.5, 1 Hz)

Example 10

Preparation of 4-amino-3-(tert-butyldimethylsilyl)butanoic acid

[Formula 11]

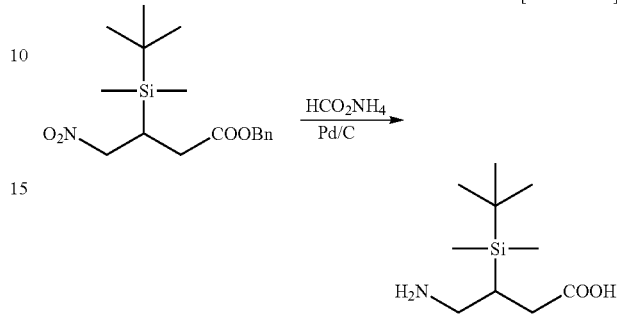

In the same manner as that of Example 9, 4-amino-3-(tert-butyldimethylsilyl)butanoic acid (173 mg, 70%) mentioned in the title was obtained as colorless powder from benzyl 4-nitro-3-(tert-butyldimethylsilyl)butanoate (386 mg, 1.15 mmol).

Mp: 163 to 164.5° C. (methanol)

MS (m/z): 184 (M$^+$-H$_2$O-Me, 3), 142 (92), 114 (68), 99 (32), 75 (100), 73 (89), 59 (78), 45 (22), 43 (35), 41 (46)

IR (KBr) cm$^{-1}$: 1653

$^1$H-NMR (CD$_3$OD) δ: 0.05 (3H, s), 0.06 (3H, s), 0.96 (911, s), 1.42 (1H, dddd, J=11.5, 11, 2, 1.5 Hz), 2.32 (1H, dd, J=16.5, 11 Hz), 2.66 (1H, ddd, J=16.5, 2, 1.5 Hz), 2.89 (1H, dd, J=13, 11.5 Hz), 3.23 (1H, ddd, J=13, 1.5, 1.5 Hz)

Example 11

Preparation of 4-amino-3-(dimethylphenylsilyl)butanoic acid

[Formula 12]

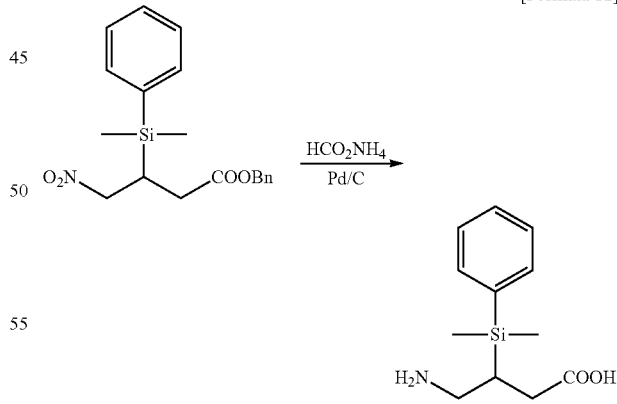

In the same manner as that of Example 9, 4-amino-3-(dimethylphenylsilyl)butanoic acid (68 mg, 41%) mentioned in the title was obtained as colorless powder from benzyl 4-nitro-3-(dimethylphenylsilyl)butanoate (250 mg, 0.70 mmol).

MS (m/z): 219 (M$^+$-H$_2$O, 6), 218 (20), 141 (23), 135 (100)

$^1$H-NMR (CD$_3$OD) δ: 0.35 (3H, s), 0.36 (3H, s), 1.50 (1H, dddd, J=11, 11, 2, 1.5 Hz), 2.25 (1H, dd, J=16.5, 11 Hz), 2.59

(1H, ddd, J=16.5, 1.5, 1.5 Hz), 2.77 (1H, dd, J=13, 11 Hz), 3.23 (1H, ddd, J=13, 1.5, 1.5 Hz), 7.32-7.42 (3H, m), 7.50-7.58 (2H,

Example 12

Preparation of 4-amino-3-(dimethyl-n-octylsilyl)butanoic acid

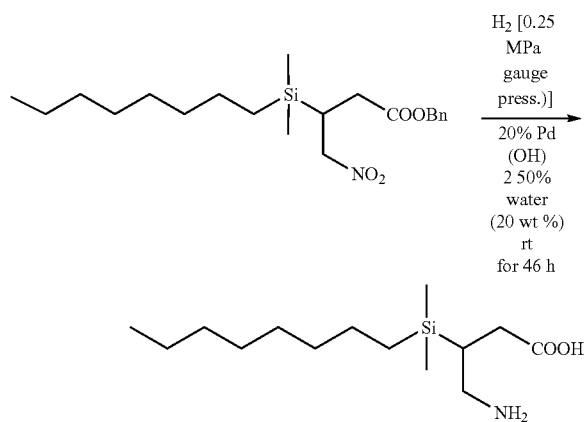

A suspension of benzyl 4-nitro-3-(dimethyl-n-octylsilyl) butanoate (220 mg, 0.560 mmol) and palladium hydroxide (20% on carbon, wetted with ca. 50% water, 44 mg) in methanol (2 ml) was subjected to catalytic reduction under a hydrogen atmosphere [0.25 MPa (gauge pressure)] for 48 hours. After the suspension was filtered through Celite, and the solvent was evaporated, the residue was washed with water and recrystallized to obtain 4-amino-3-(dimethyl-n-octylsilyl)butanoic acid mentioned in the title.

$^1$H-NMR (CD$_3$OD) δ: 0.04 (3H, s), 0.05 (3H, s), 0.50-0.65 (2H, m), 0.89 (3H, br t, J=7 Hz), 1.25-1.40 (13H, m), 2.26 (1H, dd, J=16.5, 11.5 Hz), 2.55 (1H, ddd, J=16.5, 2, 1.5 Hz), 2.82 (1H, dd, J=13, 11.5 Hz), 3.15 (1H, ddd J=13, 2, 1.5 Hz)

Example 13

Preparation of ethyl 3-(trimethylsilyl)-2-cyanopropionate

[Formula 14]

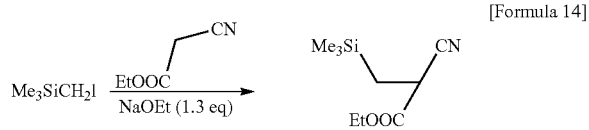

A solution of ethyl cyanoacetate (5.34 g, 47.3 mmol) in dimethyl sulfoxide (DMSO, 20 ml) was added portionwise with sodium ethoxide (3.21 g, 47.2 mmol), and the mixture was stirred at room temperature for 4 hours with occasionally cooling the mixture on ice when temperature elevation was observed. The reaction mixture was put on an ice bath, and added dropwise with a solution of iodomethyltrimethylsilane (7.78 g, 36.4 mmol) in DMSO (5 ml), and the mixture was stirred at room temperature for 24 hours. The reaction mixture was added with saturated aqueous ammonium chloride, and the mixture was extracted with ethyl acetate. The organic layer was washed with water and dried over anhydrous sodium sulfate, and the solvent was evaporated. The residue was purified by silica gel chromatography [hexane/ethyl acetate (49:1)] to obtain ethyl 3-(trimethylsilyl)-2-cyanopropionate (6.06 g, 65%) mentioned in the title as colorless oil.

IR (neat) cm$^{-1}$: 2245, 1741

$^1$H-NMR (CDCl$_3$) δ: 0.13 (9H, s), 1.22 (1H, dd, J=14.5, 8.5 Hz), 1.27 (1H, dd, J=14.5, 7 Hz), 1.33 (3H, t, J=7 Hz), 3.46 (1H, dd, J=8.5, 7 Hz), 4.26 (2H, q, J=7 Hz)

Example 14

Preparation of diethyl 2-cyano-2-(trimethylsilylmethyl)succinate

[Formula 15]

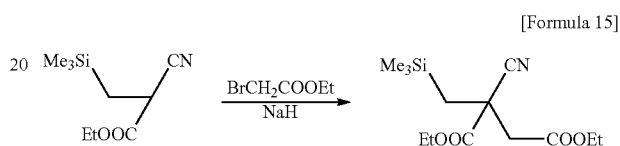

A solution of ethyl 3-(trimethylsilyl)-2-cyanopropionate (2.26 g, 11.4 mmol) obtained in Example 13 in THF (15 ml) was cooled on ice, and added with sodium hydride (60%, 473 mg, 11.8 mmol) under an argon atmosphere, and the mixture was stirred for 30 minutes. The reaction mixture was added with ethyl bromoacetate (1.39 ml, 12.5 mmol), the mixture was stirred for 30 minutes under ice cooling, and stirring was further continued at room temperature for 20 hours. The reaction mixture was added with saturated aqueous ammonium chloride, and the mixture was extracted with ethyl acetate. The organic layer was washed with water, and then dried over anhydrous sodium sulfate, and the solvent was evaporated. The residue was purified by silica gel chromatography [hexane/ethyl acetate (19:1)] to obtain diethyl 2-cyano-2-(trimethylsilylmethyl)succinate (3.22 g, 99%) mentioned in the title as colorless oil.

MS (m/z): 270 (M$^+$-Me, 10), 212 (23), 196 (29), 168 (15), 75 (32), 73 (100), 57 (16), 45 (16)

IR (neat) cm$^{-1}$: 2245, 1736

$^1$H-NMR (CDCl$_3$) δ: 0.15 (9H, s), 1.23 (1H, d, J=14.5 Hz), 1.27 (3H, t, J=7 Hz), 1.31 (1H, d, J=14.5 Hz), 1.36 (3H, t, J=7 Hz), 2.83 (1H, d, J=16.5 Hz), 3.07 (1H, d, J=16.5 Hz), 4.20 (2H, q, J=7 Hz), 4.25 (1H, dq, J=11, 7 Hz), 4.31 (1H, dq, J=11, 7 Hz)

Example 15

Preparation of ethyl 4-(trimethylsilyl)-3-cyanobutanoate

[Formula 16]

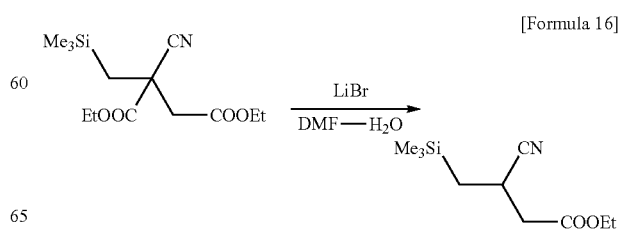

A solution of diethyl 2-cyano-2-(trimethylsilylmethyl)succinate (592 mg, 2.08 mmol) in dimethylformamide (DMF, 5 ml) was added with water (45 μl, 2.50 mmol) and lithium bromide (217 mg, 2.49 mmol), and the mixture was stirred at 150° C. for 15 hours. The reaction mixture was cooled on ice, and added with aqueous hydrochloric acid (1 N), and the mixture was extracted with ethyl acetate. The organic layer was washed with water, and then dried over anhydrous sodium sulfate, and the solvent was evaporated. The residue was purified by silica gel chromatography [hexane/ethyl acetate (14:1)] to obtain ethyl 4-trimethylsilyl-3-cyanobutanoate (404 mg, 91%) mentioned in the title as colorless oil.

HRMS: Calcd for $C_{10}H_{19}NO_2Si$: 213.1184, Found: 213.1180

MS (m/z): 213 ($M^+$, 0.6), 198 (3), 170 (15), 140 (12), 126 (20), 99 (17), 75 (41), 73 (100), 45 (20), 43 (14), 41 (21)

IR (neat) $cm^{-1}$: 2240, 1732

$^1$H-NMR ($CDCl_3$) δ: 0.13 (9H, s), 0.85 (1H, dd, J=14.5, 5 Hz), 1.01 (1H, dd, J=14.5, 10.5 Hz), 1.29 (3H, t, J=7 Hz), 2.56 (1H, dd, J=16.5, 7 Hz), 2.74 (1H, dd, J=16.5, 7.5 Hz), 3.05 (1H, dddd, J=10.5, 7.5, 7, 5 Hz), 4.20 (2H, q, J=7 Hz)

Example 16

Preparation of 4-trimethylsilyl-3-cyanobutanoic acid

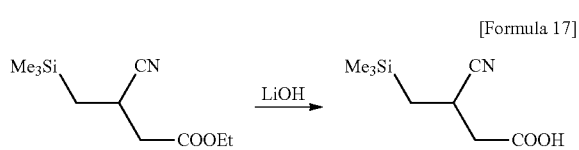 [SMILES: CCOC(=O)CC(C#N)C[Si](C)(C)C ; "LiOH" ; C[Si](C)(C)CC(C#N)CC(=O)O]

[Formula 17]

A solution of ethyl 4-(trimethylsilyl)-3-cyanobutanoate (341 mg, 1.60 mmol) in methanol/1,2-dimethoxyethane/water (3:2:1, 4.2 ml) was added with lithium hydroxide monohydrate (135 mg, 3.21 mmol), and the mixture was refluxed by heating for 1 hour with stirring. The reaction mixture was cooled on ice, and added with aqueous hydrochloric acid (1 N), and the mixture was extracted with ethyl acetate. The organic layer was washed with water and dried over anhydrous sodium sulfate, and the solvent was evaporated. The obtained crystals were purified by recrystallization, and the mother solution was subjected to purification by silica gel chromatography (2% methanol/chloroform) to obtain 4-trimethylsilyl-3-cyanobutanoic acid (295 mg, quant.) mentioned in the title as colorless scaly crystals.

Mp: 39 to 41° C. (hexane)

HRMS: Calcd for $C_8H_{15}NO_2Si$: 185.0871, Found: 185.0886

MS (m/z): 185 ($M^+$, 0.4), 170 (17), 140 (17), 126 (19), 117 (14), 99 (22), 75 (77), 73 (100), 45 (14), 43 (17)

IR (KBr) $cm^{-1}$: 2245, 1699

$^1$H-NMR ($CD_3OD$) δ: 0.12 (9H, s), 0.91 (1H, dd, J=14.5, 5 Hz), 1.01 (1H, dd, J=14.5, 10.5 Hz), 2.61 (1H, dd, J=16.5, 6.5 Hz), 2.71 (1H, dd, J=16.5, 7.5 Hz), 3.06 (1H, dddd, J=10.5, 7.5, 6.5, 5 Hz)

Example 17

Preparation of 4-amino-3-(trimethylsilylmethyl)butanoic acid

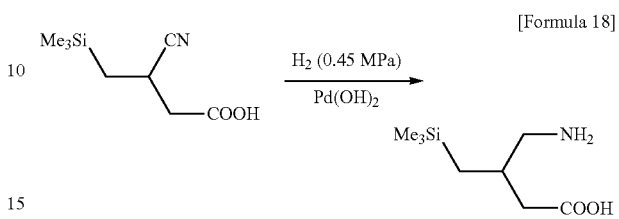

[Formula 18]

A suspension of 4-(trimethylsilyl)-3-cyanobutanoic acid (178 mg, 0.962 mmol) and palladium hydroxide (20% on carbon, wetted with ca. 50% water, 36 mg) in methanol (10 ml) was subjected to catalytic reduction under a hydrogen atmosphere [0.45 MPa (gauge pressure)] for 48 hours. The reaction mixture was filtered through Celite, the solvent was evaporated, and then the residue was recrystallized to obtain 4-amino-3-(trimethylsilylmethyl)butanoic acid (172 mg, 95%) mentioned in the title as colorless fine prism crystals.

Mp: 167 to 168° C. (methanol/2-propanol)

HRMS: Calcd for $C_8H_{19}NO_2Si$: 189.1184, Found: 189.1195

MS (m/z): 189 ($M^+$, 0.7), 170 (10), 156 (21), 75 (43), 73 (100), 59 (16), 45 (26), 43 (21), 41 (30)

IR (KBr) $cm^{-1}$: 2175, 1651

$^1$H-NMR ($CD_3OD$) δ: 0.07 (9H, s), 0.61 (1H, dd, J=15, 6 Hz), 0.69 (1H, dd, J=15, 8.5 Hz), 2.10-2.23 (1H, m), 2.29 (1H, dd, J=15.5, 9 Hz), 2.46 (1H, dd, J=15.5, 3 Hz), 2.85 (1H, dd, J=12.5, 7.5 Hz), 2.92 (1H, dd, J=12.5, 4 Hz)

Example 18

Preparation of benzyl 3-(1-methyl-1-silacyclohexan-1-yl)acrylate

A suspension of metal magnesium (776 mg, 32.3 mg atom) in THF (15 ml) was added with ethyl bromide (2.41 ml, 32.3 mmol) under ice cooling, and the mixture was stirred at room temperature for 15 minutes and at 45 to 50° C. for 30 minutes. The reaction mixture was cooled on ice, and added with a solution of 2-(2-propynyloxy)tetrahydropyran (4.48 ml, 32.3 mmol) in THF (5 ml), and the mixture was stirred at 0° C. to room temperature for 16 hours. The reaction mixture was cooled on ice, and added with a solution of 1-chloro-1-methyl-1-silacyclohexane (2.40 g, 16.2 mmol) in THF (5 ml), the mixture was stirred for 5 minute, and stirring was further continued at room temperature for 10 minutes and under reflux by heating for 2 hours. The reaction mixture was cooled on ice, and added with saturated ammonium chloride, and the mixture was extracted with ethyl acetate. The organic layer was treated in a conventional manner, and the residue was purified by silica gel chromatography [hexane/ethyl acetate (79:1 to 59:1 to 9:1)] to obtain colorless oil (3.919 g, 96%). A part of this product (3.120 g, 12.4 mmol) was dissolved in methanol/dimethoxyethane (1:1, 8 ml), the solution was added with 10% aqueous hydrochloric acid (4 ml), and the mixture was stirred at room temperature for 29 hours. The reaction mixture was added portionwise with saturated aqueous sodium hydrogencarbonate and thereby neutralized, and the mixture was extracted with ethyl acetate. The organic layer was treated in a conventional manner, and the residue was purified by silica gel chromatography [hexane/ethyl acetate (19:1)] to obtain colorless oil (1.705 g, 82%). A part of this product (1.702 g, 10.1 mmol) was subjected to the three steps of Example 2 in the same manner, and then the resultant was purified by silica gel chromatography [hexane/ethyl acetate (49:1)] to obtain benzyl 3-(1-methyl-1-silacyclohexan-1-yl)acrylate (2.152 g, 78% in total for three steps) mentioned in the title as colorless oil.

HRMS: Calcd for $C_{16}H_{22}O_2Si$: 274.1388, Found: 274.1371

MS (m/z): 274 (M⁺, 12), 259 (2), 231 (7), 183 (11), 167 (11), 144 (28), 113 (21), 91 (100), 85 (26), 43 (23)

IR (neat) cm⁻¹: 1718

¹H-NMR, (CDCl₃) δ: 0.13 (3H, s), 0.58-0.70 (2H, m), 0.71-0.82 (2H, m), 1.32-1.50 (2H, m), 1.60-1.76 (4H, m), 5.20 (2H, s), 6.34 (1H, d, J=19 Hz), 7.32-7.43 (5H, m), 7.34 (1H, d, J=19 Hz)

Example 19

Preparation of benzyl 4-nitro-3-(1-methyl-1-silacyclohexan-1-yl)butanoate

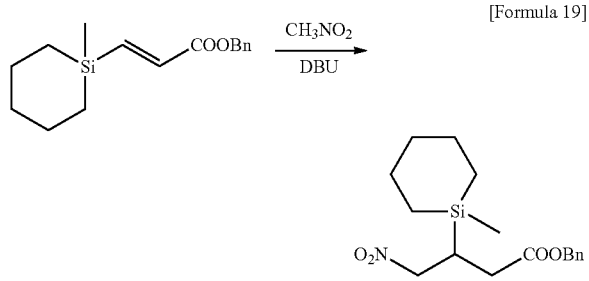

[Formula 19]

A solution of benzyl 3-(1-methyl-1-silacyclohexan-1-yl) acrylate (1.940 g, 7.08 mmol) in nitromethane (5 ml) was cooled on ice, and added with DBU (0.26 ml, 1.74 mmol), and the mixture was stirred for 30 minutes, and further stirred at room temperature for 17 hours. The reaction mixture was added with aqueous hydrochloric acid (1 N), the mixture was extracted with ethyl acetate, and the organic layer was washed with saturated aqueous sodium hydrogencarbonate, and then treated in a conventional manner. The residue was purified by silica gel column chromatography [hexane/ethyl acetate (14:1)] to obtain benzyl 4-nitro-3-(1-methyl-1-silacyclohexan-1-yl)butanoate (1.711 g, 72%) mentioned in the title as colorless oil.

MS (m/z): 289 (M⁺-NO₂, 0.3), 249 (0.2), 201 (1), 173 (1), 113 (5), 101 (6), 91 (100), 85 (7), 61 (4), 43 (5)

IR (neat) cm⁻¹: 1730, 1547

¹H-NMR (CDCl₃) δ: 0.08 (3H, s), 0.53-0.73 (4H, m), 1.18-1.31 (1H, m), 1.44-1.59 (3H, m), 1.73-1.86 (2H, m), 2.08 (1H, dddd, J=9, 6.5, 6, 5 Hz), 2.49 (1H, dd, J=16.5, 6.5 Hz), 2.56 (1H, dd, J=16.5, 6 Hz), 4.46 (1H, dd, J=13, 5 Hz), 4.51 (1H, dd, J=13, 9 Hz), 5.09 (1H, d, J=12.5 Hz), 5.13 (1H, d, J=12.5 Hz), 7.31-7.41 (5H, m)

Example 20

Preparation of 4-amino-3-(1-methyl-1-silacyclohexan-1-yl)butanoic acid

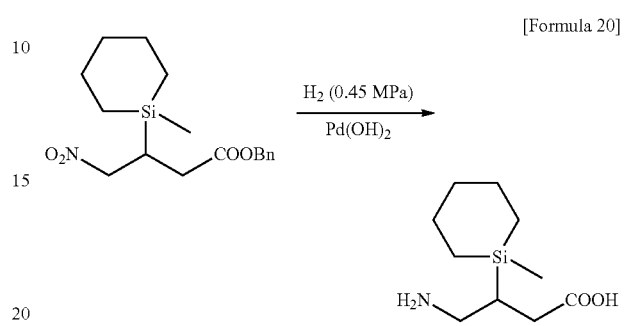

[Formula 20]

A suspension of benzyl 3-(1-methyl-1-silacyclohexan-1-yl)acrylate (1.680 g, 5.01 mmol) and Pd(OH)₂ (20% on carbon, wetted with ca. 50% water, 168 mg) in methanol (30 ml) was subjected to catalytic reduction at room temperature for 48 hours under a hydrogen atmosphere [0.45 MPa (gauge pressure)]. The reaction mixture was filtered through Celite, the solvent was evaporated, and the residue was recrystallized to obtain 4-amino-3-(1-methyl-1-silacyclohexan-1-yl)butanoic acid (477 mg, 44%) mentioned in the title as colorless prism crystals.

Mp: 160 to 161.5° C. (methanol/2-propanol)

HRMS: Calcd for $C_{10}H_{21}NO_2Si$: 215.1340, Found: 215.1350

MS (m/z): 215 (M⁺, 0.4), 214 (2), 198 (20), 197 (19), 196 (46), 168 (14), 155 (31), 113 (66), 85 (100), 59 (43), 45 (32), 43 (57), 41 (33)

IR (neat) cm⁻¹: 1636

¹H-NMR (CD₃OD) δ: 0.60 (3H, s), 0.65-0.73 (4H, m), 1.25-1.39 (1H, m), 1.33 (1H, dddd, J=11.5, 11, 2.5, 2 Hz), 1.47-1.66 (3H, m), 1.75-1.90 (2H, m), 2.27 (1H, dd, 11 Hz), 2.54 (1H, ddd, J=16.5, 2.5, 1 Hz), 2.83 (1H, dd, 11.5 Hz), 3.14 (1H, ddd, J=13, 2, 1 Hz)

Example 21

Preparation of ethyl 3-[(1-methyl-1-silacyclopentan-1-yl)methyl]-2-cyanopropionate

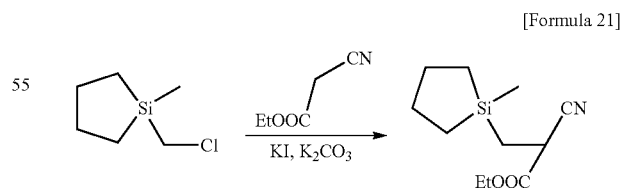

[Formula 21]

A solution of 1-chloromethyl-1-methyl-1-silacyclopentane (1.500 g, 10.1 mmol) and ethyl cyanoacetate (1.29 ml, 12.1 mmol) in acetonitrile (25 ml) was added with potassium iodide (2.01 g, 12.1 mmol) and potassium carbonate (2.09 g, 15.1 mmol), and the mixture was stirred for 38 hours under reflux by heating. The reaction vessel was cooled on ice, the reaction mixture was added with saturated aqueous ammonium chloride, and the mixture was extracted with ethyl acetate. The organic layer was treated in a conventional manner, and the residue was purified by silica gel column chromatography [hexane/ethyl acetate (9:1)] to obtain ethyl 3-[(1-methyl-1-silacyclopentan-1-yl)methyl]-2-cyanopropionate (1.449 g, 64%) as colorless oil.

IR (neat) cm$^{-1}$: 2245, 1740

$^1$H-NMR (CDCl$_3$) δ: 0.21 (3H, s), 0.55-0.76 (4H, m), ca. 1.30-1.38 (2H, m), 1.33 (3H, dd, J=7, 7 Hz), 1.57-1.63 (4H, m), 3.50 (1H, dd, J=8.5, 7 Hz), 4.21-4.31 (2H, m)

Example 22

Preparation of ethyl 3-[(1-methyl-1-silacyclohexan-1-yl)methyl]-2-cyanopropionate

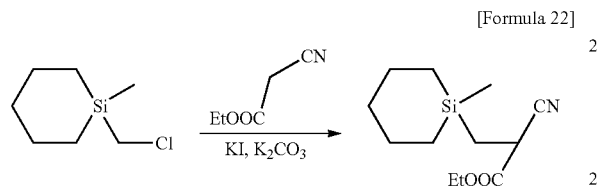

[Formula 22]

1-Chloromethyl-1-methyl-1-silacyclohexane (1.892 g, 11.6 mmol) was condensed with ethyl cyanoacetate in the same manner as that of Example 21 mentioned above, the reaction mixture was treated in a conventional manner, and the residue was purified by silica gel column chromatography [hexane/ethyl acetate (9:1)] to obtain ethyl 3-[(1-methyl-1-silacyclohexan-1-yl)methyl]-2-cyanopropionate (2.185 g, 79%) mentioned in the title as colorless oil.

IR (neat) cm$^{-1}$: 2240, 1741

$^1$H-NMR (CDCl$_3$) δ: 0.15 (3H, s), 0.63-0.76 (4H, m), ca. 1.25-1.31 (2H, m), 1.33 (3H, dd, J=7, 7 Hz), ca. 1.33-1.52 (2H, m), 1.58-1.79 (4H, m), 3.47 (1H, dd, J=8.5, 7 Hz), 4.20-4.31 (2H, m)

Example 23

Preparation of diethyl 2-cyano-2-[(1-methyl-1-silacyclopentan-1-yl)methyl] succinate

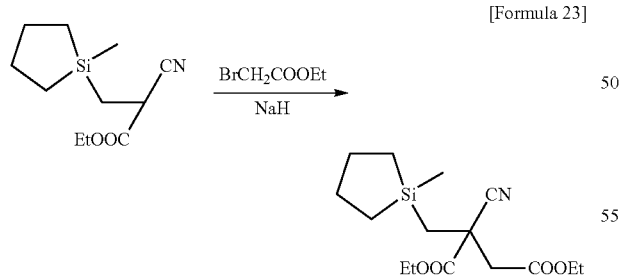

[Formula 23]

Ethyl 3-[(1-methyl-1-silacyclopentan-1-yl)methyl]-2-cyanopropionate (1.432 g, 6.36 mmol) was condensed with ethyl bromoacetate in the same manner as that of Example 14 mentioned above, the reaction mixture was treated in a conventional manner, and the residue was purified by silica gel column chromatography [hexane/ethyl acetate (8:1)] to obtain diethyl 2-cyano-2-[(1-methyl-1-silacyclopentan-1-yl)methyl]succinate (1.958 g, 99%) mentioned in the title as colorless viscous oil.

HRMS: Calcd for C$_{15}$H$_{25}$NO$_4$Si: 311.1551, Found: 311.1549

MS (m/z): 311 (M$^+$, 2), 296 (4), 282 (37), 266 (13), 238 (100), 210 (68), 208 (31), 196 (23), 185 (27), 99 (49), 71 (33), 43 (34)

IR (neat) cm$^{-1}$: 2240, 1735

$^1$H-NMR (CDCl$_3$) δ: 0.28 (3H, s), 1.55-1.62 (4H, m), 1.27 (3H, t, J=7 Hz), 1.34 (1H, d, J=15 Hz), 1.36 (3H, dd, J=7, 7 Hz), 1.40 (1H, d, J=15 Hz), 1.55-1.62 (4H, m), 2.83 (1H, d, J=17 Hz), 3.08 (1H, d, J=17 Hz), 4.19 (2H, q, J=7 Hz), 4.26 (1H, dq, J=11, 7 Hz), 4.31 (1H, dq, J=11, 7 Hz)

Example 24

Preparation of diethyl 2-cyano-2-[(1-methyl-1-silacyclohexan-1-yl)methyl]succinate

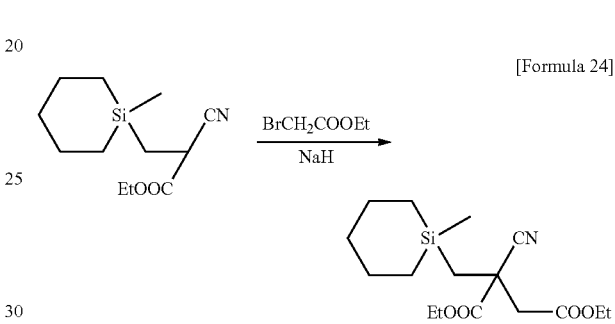

[Formula 24]

Ethyl 3-[(1-methyl-1-silacyclohexan-1-yl)methyl]-2-cyanopropionate (2.167 g, 9.07 mmol) was condensed with ethyl bromoacetate in the same manner as that of Example 14, the reaction mixture was treated in a conventional manner, and the residue was purified by silica gel column chromatography [hexane/ethyl acetate (10:1)] to obtain diethyl 2-cyano-2-[(1-methyl-1-silacyclohexan-1-yl)methyl]succinate (2.828 g, 96%) mentioned in the title as colorless viscous oil.

HRMS: Calcd for C$_{16}$H$_{27}$NO$_4$Si: 325.1708, Found: 325.1722

MS (m/z): 325 (M$^+$, 4), 310 (5), 296 (24), 282 (55), 252 (100), 224 (35), 208 (68), 113 (48), 85 (80), 59 (38), 45 (19), 43 (44)

IR (neat) cm$^{-1}$: 2240, 1734

$^1$H-NMR (CDCl$_3$) δ: 0.20 (3H, s), 0.65-0.75 (4H, m), 1.27 (1H, d, J=15 Hz), 1.27 (3H, t, J=7 Hz), 1.35 (1H, d, J=15 Hz), 1.36 (3H, dd, J=7, 7 Hz), 1.43-1.66 (4H, m), 1.66-1.83 (2H, m), 2.83 (1H, d, J=17 Hz), 3.06 (1H, d, J=17 Hz), 4.19 (2H, q, J=7 Hz), 4.25 (1H, dq, J=11, 7 Hz), 4.31 (1H, dq, J=11, 7 Hz)

Example 25

Preparation of ethyl 4-(1-methyl-1-silacyclopentan-1-yl)-3-cyanobutanoate

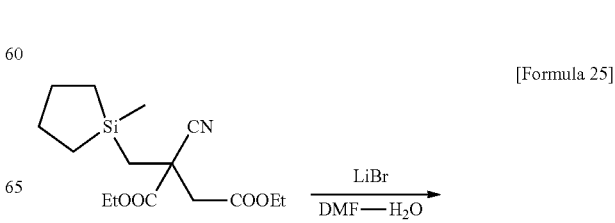

[Formula 25]

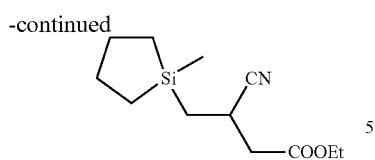

Diethyl 2-cyano-2-[(1-methyl-1-silacyclopentan-1-yl)methyl]succinate (1.943 g, 6.25 mmol) was treated with water and lithium bromide in dimethylformamide in the same manner as that of Example 15. The reaction mixture was treated in a conventional manner, and the residue was purified by silica gel column chromatography [hexane/ethyl acetate (14:1)] to obtain ethyl 4-(1-methyl-1-silacyclopentan-1-yl)-3-cyanobutanoate (1.321 g, 88%) mentioned in the title was obtained as colorless oil.

HRMS: Calcd for $C_{12}H_{21}NO_2Si$: 239.1340, Found: 239.1326

MS (m/z): 239 (M$^+$, 2), 210 (39), 197 (42), 183 (40), 182 (39), 142 (32), 128 (100), 99 (89), 71 (42), 45 (28), 43 (57)

IR (neat) cm$^{-1}$: 2240, 1731

$^1$H-NMR (CDCl$_3$) δ: 0.21 (3H, s), 0.54-0.79 (4H, m), 0.97 (1H, dd, J=14.5, 5.5 Hz), 1.10 (1H, dd, J=14.5, 10 Hz), 1.29 (3H, t, J=7 Hz), 1.57-1.64 (4H, m), 2.56 (1H, dd, J=16.5, 7 Hz), 2.74 (1H, dd, J=16.5, 7 Hz), 3.09 (1H, dddd, J=10, 7, 7, 5.5 Hz), 4.20 (2H, q, J=7 Hz)

Example 26

Preparation of ethyl 4-(1-methyl-1-silacyclohexan-1-yl)-3-cyanobutanoate

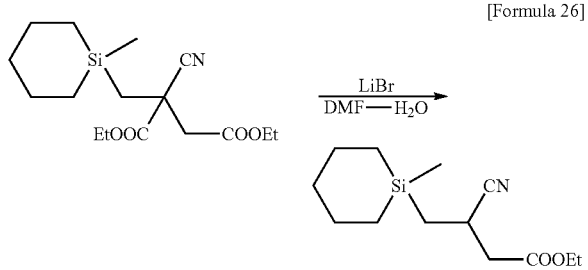

[Formula 26]

Diethyl 2-cyano-2-[(1-methyl-1-silacyclohexan-1-yl)methyl]succinate (2.814 g, 8.66 mmol) was treated in the same manner as that of Example 15 mentioned above, and then the reaction mixture was treated in a conventional manner. Then, the residue was purified by silica gel column chromatography [hexane/ethyl acetate (14:1)] to obtain ethyl 4-(1-methyl-1-silacyclohexan-1-yl)-3-cyanobutanoate (1.678 g, 77%) mentioned in the title as colorless oil.

HRMS: Calcd for $C_{13}H_{23}NO_2Si$: 253.1497, Found: 253.1508

MS (m/z): 253 (M$^+$, 10), 224 (12), 210 (90), 197 (46), 182 (76), 128 (46), 113 (91), 85 (100), 59 (46), 43 (55)

IR (neat) cm$^{-1}$: 2240, 1732

$^1$H-NMR (CDCl$_3$) δ: 0.16 (3H, s), 0.63-0.77 (4H, m), 0.91 (1H, dd, J=14.5, 5 Hz), 1.05 (1H, dd, J=14.5, 10.5 Hz), 1.29 (3H, t, J=7 Hz), 1.32-1.52 (2H, m), 1.52-1.79 (4H, m), 2.55 (1H, dd, J=16, 7 Hz), 2.74 (1H, dd, J=16, 7 Hz), 3.05 (1H, dddd, J=10.5, 7, 7, 5 Hz), 4.20 (2H, q, J=7 Hz)

Example 27

Preparation of 4-(1-methyl-1-silacyclopentan-1-yl)-3-cyanobutanoic acid

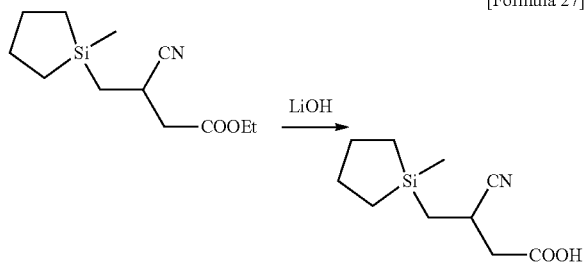

[Formula 27]

Ethyl 4-(1-methyl-1-silacyclopentan-1-yl)-3-cyanobutanoate (1.306 g, 5.46 mmol) was hydrolyzed with lithium hydroxide in the same manner as that of Example 16, and then the reaction mixture was treated in a conventional manner. The residue was purified by silica gel column chromatography (2% methanol/chloroform) to obtain 4-(1-methyl-1-silacyclopentan-1-yl)-3-cyanobutanoic acid (1.158 g, quant.) mentioned in the title as colorless oil.

HRMS: Calcd for $C_{10}H_{17}NO_2Si$: 211.1028, Found: 211.1035

MS (m/z): 211 (M$^+$, 2), 196 (6), 182 (30), 169 (22), 155 (18), 128 (100), 99 (49), 71 (27), 61 (30), 45 (30), 43 (46)

IR (neat) cm$^{-1}$: 2245, 1713

$^1$H-NMR (CDCl$_3$) δ: 0.22 (3H, s), 0.56-0.79 (4H, m), 1.00 (1H, dd, J=14.5, 5.5 Hz), 1.14 (1H, dd, J=14.5, 10 Hz), 1.56-1.66 (4H, m), 2.64 (1H, dd, J=17, 6.5 Hz), 2.82 (1H, dd, J=17, 7.5 Hz), 3.07 (1H, dddd, J=10, 7.5, 6.5, 5.5 Hz)

Example 28

Preparation of 4-(1-methyl-1-silacyclohexan-1-yl)-3-cyanobutanoic acid

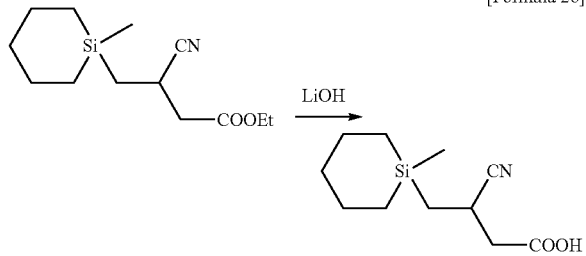

[Formula 28]

Ethyl 4-(1-methyl-1-silacyclohexan-1-yl)-3-cyanobutanoate (1.613 g, 6.38 mmol) was hydrolyzed in the same manner as that of Example 16, and the resultant was purified by silica gel column chromatography (2% methanol/chloroform) to obtain 4-(1-methyl-1-silacyclohexan-1-yl)-3-cyanobutanoic acid (1.358 g, 95%) mentioned in the title as colorless oil.

HRMS: Calcd for $C_{11}H_{19}NO_2Si$: 225.1184, Found: 225.1199

MS (m/z): 225 (M⁺, 9), 210 (7), 182 (100), 169 (46), 155 (25), 138 (56), 128 (74), 113 (65), 85 (90), 61 (42), 59 (38), 43 (63)

IR (neat) cm⁻¹: 2240, 1712

¹H-NMR (CDCl₃) δ: 0.17 (3H, s), 0.64-0.77 (4H, m), 0.93 (1H, dd, J=14.5, 5 Hz), 1.08 (1H, dd, J=14.5, 10.5 Hz), 1.29-1.53 (2H, m), 1.56-1.80 (4H, m), 2.64 (1H, dd, J=17, 6.5 Hz), 2.82 (1H, dd, J=17, 7.5 Hz), 3.04 (1H, dddd, J=10.5, 7.5, 6.5, 5 Hz)

Example 29

Preparation of 4-amino-3-[(1-methyl-1-silacyclopentan-1-yl)methyl]butanoic acid

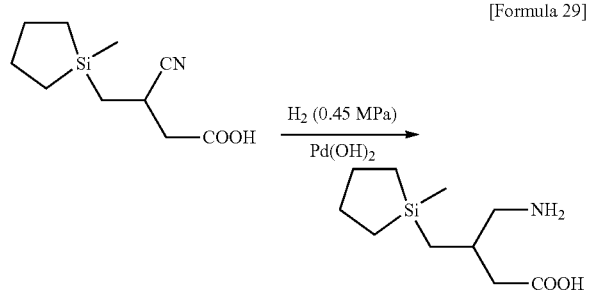

[Formula 29]

4-(1-Methyl-1-silacyclopentan-1-yl)-3-cyanobutanoic acid (555 mg, 2.63 mmol) was subjected to catalytic reduction in the presence of Pd(OH)₂ in the same manner as that of Example 20, the solvent was evaporated, and the residue was recrystallized to obtain 4-amino-3-[(1-methyl-1-silacyclopentan-1-yl)methyl]butanoic acid (274 mg, 48%) mentioned in the title as colorless powdery crystals.

Mp: 133 to 135° C. (methanol/2-propanol)

MS (m/z): 197 (M⁺-H₂O, 10), 186 (25), 168 (0), 113 (34), 99 (100), 85 (39), 71 (64), 45(56), 43 (61), 41 (48)

IR (KBr) cm⁻¹: 1652

¹H-NMR (CD₃OD) δ: 0.15 (3H, s), 0.53-0.70 (4H, m), 0.73 (1H, dd, J=14.5, 6 Hz), 0.80 (1H, dd, J=14.5, 8 Hz), 1.56-1.64 (4H, m), 2.15-2.26 (1H, m), 2.30 (1H, dd, J=15.5, 8.5 Hz), 2.47 (1H, dd, J=15.5, 3 Hz), 2.87 (1H, dd, J=12.5, 7 Hz), 2.93 (1H, dd, J=12.5, 4 Hz)

Example 30

Preparation of 4-amino-3-[(1-methyl-1-silacyclohexan-1-yl)methyl]butanoic acid

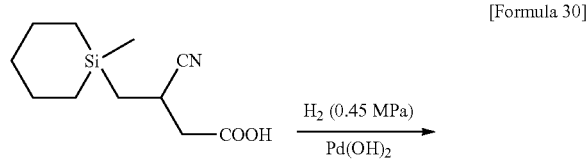

[Formula 30]

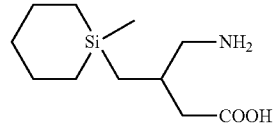

4-(1-Methyl-1-silacyclohexan-1-yl)-3-cyanobutanoic acid (597 mg, 2.65 mmol) was catalytically reduced for 72 hours in the same manner as that of Example 20 mentioned above, the solvent was evaporated, and the residue was recrystallized to obtain 4-amino-3-[(1-methyl-1-silacyclohexan-1-yl)methyl]butanoic acid (226 mg, 37%) mentioned in the title as colorless powdery crystals.

Mp: 140.5 to 143° C. (methanol/2-propanol)

MS (m/z): 211 (M⁺-H₂O, 5), 200 (12), 187 (18), 168 (38), 113 (55), 85 (100), 59 (42), 45(27), 43 (47), 41 (34)

IR (KBr) cm⁻¹: 1650

¹H-NMR (CD₃OD) δ: 0.11 (3H, s), 0.60-0.77 (6H, m), 1.28-1.83 (6H, m), 2.12-2.24 (1H, m), 2.29 (1H, dd, J=15.5, 9 Hz), 2.46 (1H, dd, J=15.5, 3.5 Hz), 2.85 (1H, dd, J=12.5, 7.5 Hz), 2.92 (1H, dd, J=12.5, 4 Hz)

Example 31

Preparation of (+)-4-amino-3-(trimethylsilylmethyl)butanoic acid and (−)-4-amino-3-(trimethylsilylmethyl)butanoic acid Ethyl (±)-4-(trimethylsilyl)-3-cyanobutanoate (2.06 g 9.67 mmol) obtained in Example 15 mentioned above was enzymatically hydrolyzed with Novozym 435 (81 mg) in a mixed solution of 0.1 M phosphate buffer (45 ml) and DMSO (9 ml) to obtain a carboxylic acid (836 mg, 42%) and the unreacted ester compound (858 mg, 47%). A part of the resulting carboxylic acid (825 mg, 4.46 mmol) was dissolved in dichloromethane (30 ml), the solution was added with DMAP (54 mg, 0.446 mmol) and EDCI (1.02 g, 5.35 mmol) at 0° C. with stirring, the mixture was stirred for one whole day and night and then treated in a conventional manner, and thereby the carboxylic acid was returned to the ethyl ester compound (824 mg, 87%). This ester compound of which optical purity was increased (824 mg, 3.87 mmol) was hydrolyzed again with Novozym 435 in the same manner as that mentioned above to obtain a carboxylic acid (366 mg, 51%). A part of this carboxylic acid (250 mg, 1.35 mmol) was catalytically reduced in the same manner as that of Example 17 mentioned above, and the resultant was recrystallized to obtain (−)-4-amino-3-(trimethylsilylmethyl)butanoic acid (41 mg, 16%).

A part of 858 mg of the unreacted ester compound obtained above (831 mg, 3.90 mmol) was hydrolyzed in the same manner as that of Example 16 mentioned above and thereby made into a carboxylic acid (702 mg, 97%). This carboxylic acid was catalytically reduced in the same manner as that of Example 17 mentioned above, and the resultant was recrystallized to obtain (+)-4-amino-3-(trimethylsilylmethyl)butanoic acid (229 mg, 32%).

(−)-4-Amino-3-(trimethylsilylmethyl)butanoic acid

Mp: 186 to 187° C. (cap.) (methanol/2-propanol)

$[\alpha]^{25}D$−25.3 (c 1.00, methanol)

(+)-4-Amino-3-(trimethylsilylmethyl)butanoic acid

Mp: 185 to 186° C. (cap.) (methanol/2-propanol).

$[\alpha]^{25}D$+26.0 (c 1.00, methanol)

Test Example 1

Binding to Gabapentin Receptor

According to the method of Suman-Chauhan et al. (Eur. J. Pharmacol, 244 (3), pp. 293-301, 1993), a gabapentin receptor was prepared from the brains of Wister rats. Binding of the following compounds (1 μM) to the gabapentin receptor was investigated on the basis of inhibition of binding of gabapentin in the presence of 0.02 μM [$^3$H] gabapentin. As a result, the following inhibition ratios were observed.

4-Amino-3-(trimethylsilyl)butanoic acid: 35%
4-Amino-3-(t-butyldimethylsilyl)butanoic acid: 13%
4-Amino-3-(trimethylsilylmethyl)butanoic acid: 28%
4-Amino-3-(dimethyl-n-octylsilyl)butanoic acid: 32%

Test Example 2

Analgesic Action Test Using Chung Model

A rat Chung model was used. 4-Amino-3-(trimethylsilyl)butanoic acid (Compound A), 4-amino-3-(trimethylsilylmethyl)butanoic acid (Compound B), 4-amino-3-[(1-methyl-1-silacyclopentan-1-yl)methyl]butanoic acid (Compound C), 4-(1-methyl-1-silacyclohexan-1-yl)-3-cyanobutanoic acid (Compound D), and pregabalin (positive control, Compound E) were each orally administered once to the rats, and analgesic action was examined 30 minutes thereafter on the basis of pain threshold values obtained with a physical stimulation (total number of groups: 11, N=6). As a result, the pain threshold values (g) of the agent-administered groups and the control group were as follows.

Control (0.5% MC): 5.3±0.4
Compound A: 7.8±0.5 (60 mg/kg), 6.2±0.4 (20 mg/kg)
Compound B: 7.9±0.4 (60 mg/kg), 5.4±0.2 (20 mg/kg)
Compound C: 8.8±0.3 (60 mg/kg), 5.7±0.6 (20 mg/kg)
Compound D: 7.3±0.5 (60 mg/kg), 4.8±0.2 (20 mg/kg)
Compound E: 8.3±0.2 (30 mg/kg), 6.3±0.3 (10 mg/kg)

What is claimed is:

1. A compound represented by the following formula (I), or a salt thereof:

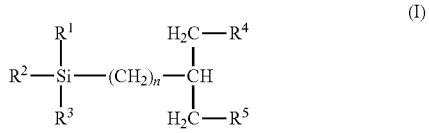

wherein, in the formula, $R^1$, $R^2$, and $R^3$ independently represent an alkyl group, an alkenyl group, an alkynyl group, or an aryl group, any of which may have a substituent, and wherein two or three groups selected from $R^1$, $R^2$, and $R^3$ may bind together to form a ring;

n represents 0 or 1;

$R^4$ represents an unsubstituted amino group, a monoalkylamino group, or an acylamino group; and $R^5$ represents —$(CY_2)_p$—$COOR^6$ wherein p represents an integer of 0 to 3, Y represents a hydrogen atom or deuterium atom, and $R^6$ represents a hydrogen atom or an alkyl group that may have a substituent.

2. The compound or a salt thereof according to claim 1, wherein $R^1$, $R^2$, and $R^3$ are independently an alkyl group or an aryl group, and wherein two or three groups selected from $R^1$, $R^2$, and $R^3$ may bind together to form a ring;

n is 0 or 1;

and $R^5$ is —$(CH_2)_p$—$COOR^6$ wherein p represents an integer of 0 to 3, and $R^6$ is a hydrogen atom or an alkyl group.

3. The compound or a salt thereof according to claim 1, wherein $R^1$, $R^2$, and $R^3$ are independently an alkyl group, in which two or three groups selected from $R^1$, $R^2$, and $R^3$ may bind together to form a ring;

n is 0;

and $R^5$ is —$(CH_2)$p-$COOR^6$ wherein p is 1, and $R^6$ is a hydrogen atom or an alkyl group.

* * * * *